(12) United States Patent
Fang

(10) Patent No.: US 8,586,304 B2
(45) Date of Patent: Nov. 19, 2013

(54) METHOD FOR DETECTING AND QUANTIFYING POLY(A) RNA AND MRNA

(75) Inventor: Nan Fang, Hilden (DE)

(73) Assignee: Qiagen GmbH, Hilden (DE)

( * ) Notice: Subject to any disclaimer, the term of this patent is extended or adjusted under 35 U.S.C. 154(b) by 0 days.

(21) Appl. No.: 13/504,377

(22) PCT Filed: Dec. 1, 2010

(86) PCT No.: PCT/EP2010/068663
§ 371 (c)(1), (2), (4) Date: Apr. 26, 2012

(87) PCT Pub. No.: WO2011/067299
PCT Pub. Date: Jun. 9, 2011

(65) Prior Publication Data
US 2012/0219953 A1    Aug. 30, 2012

(30) Foreign Application Priority Data

Dec. 4, 2009 (DE) .......... 10 2009 056 729

(51) Int. Cl.
| C12Q 1/68 | (2006.01) |
| C12P 19/34 | (2006.01) |
| C12M 1/34 | (2006.01) |
| C07H 19/00 | (2006.01) |
| C07H 21/02 | (2006.01) |
| C07H 21/04 | (2006.01) |

(52) U.S. Cl.
USPC ....... 435/6.1; 435/6.11; 435/91.1; 435/91.51; 435/287.2; 536/22.1; 536/23.1; 536/24.3

(58) Field of Classification Search
USPC ............. 435/6.1, 6.11, 91.1, 91.51, 287.2; 536/22.1, 23.1, 24.3
See application file for complete search history.

(56) References Cited

U.S. PATENT DOCUMENTS

| 5,599,672 A | * | 2/1997 | Liang et al. ................ 435/6.12 |
| 5,976,797 A | | 11/1999 | Mitsuhashi |
| 2004/0076994 A1 | | 4/2004 | Yaku et al. |

OTHER PUBLICATIONS

Wong Marisa L. et al.: "Real-time PCR for mRNA quantitation"; Biotechniques, Informa Life Sciences Publishing, Westborough, MA; vol. 39, No. 1; Jul. 1, 2005; pp. 75-85; XP002556339.

* cited by examiner

Primary Examiner — Narayan Bhat
(74) Attorney, Agent, or Firm — Rankin, Hill & Clark LLP

(57) ABSTRACT

The present invention relates to a method for detecting and/or for quantifying poly(A) RNA and/or mRNA, wherein a poly (dT) oligonucleotide which features a fluorescent dye and also a quencher is hybridized to the nucleic acid to be detected. Non-hybridized poly(dT) oligonucleotide is degraded by an added nuclease, and as a result, fluorescently labelled nucleotides are released and the resulting fluorescent signal is measured.

15 Claims, 2 Drawing Sheets

METHOD FOR DETECTING AND QUANTIFYING POLY(A) RNA AND MRNA

BACKGROUND OF INVENTION

1. Field of Invention

The present invention relates to a method for detecting and/or for quantifying poly(A) RNA and/or mRNA, wherein a poly(dT) oligonucleotide which comprises a fluorescent dye and also a quencher is hybridized to the nucleic acid to be detected. Non-hybridized poly(dT) oligonucleotide is degraded by an added nuclease, and as a result, fluorescently labelled nucleotides are released and the resulting fluorescent signal is measured.

2. Description of Related Art

The quantification of the exact amount of mRNA added is of great importance for many methods in molecular biology. More particularly for various gene expression analyses, such as, for example, quantitiative reverse-transcription PCR (qRT-PCR) and microarrays, this so-called normalization is important for obtaining accurate and comparable experimental results.

The amount of RNA added is usually determined by means of spectrophotometry by measuring the absorbance at 260 nm. This technique, however, has the disadvantage that, at this wavelength, not only the mRNA but also further nucleic acids, such as DNA, rRNA, tRNA and further non-coding RNAs, are detected, i.e. the exact amount of mRNA present is not known.

For this reason, the DNA is generally removed from the sample by means of a purification method prior to the quantification of the RNA, meaning additional process steps and costs. After the removal of the DNA, the amount of total RNA is determined in a spectrophotometer and, from this, the amount of mRNA present is indirectly deduced. Since, however, the ratio of mRNA to total RNA is not constant, but can be completely different from preparation to preparation and also in different starting materials, a high error rate arises when the total RNA is used to deduce the amount of the mRNA present.

A further disadvantage of this method is that it cannot be established whether the mRNA in the sample has already (partially) been degraded. The degradation of mRNAs often begins with the removal of the poly(A) tail at the 3' end and continues with the degradation of the coding region. Such mRNA is no longer intact and often no longer usable for molecular biology experiments.

In order to be able to add intact, quantifiable total mRNA to a molecular biology reaction, this mRNA first has to be purified from the biological sample in a time-consuming and multi-step procedure with the aid of poly(dT) nucleotides coupled to a solid phase. This procedure is, however, not quantitative, and so, during the purification procedure, some of the mRNA from the biological sample is lost. After the purification, the mRNA thus isolated has to be quantified spectrophotometrically, meaning not only an additional process step but also a loss of some of the isolated mRNA.

BRIEF SUMMARY OF THE INVENTION

An object of the present invention is to overcome the disadvantages of the methods known in the prior art and to provide an inexpensive and less time-consuming method for specifically detecting and/or for quantifying mRNA and poly(A) RNA, wherein the total RNA does not first have to be removed from the mRNA fraction.

This object is achieved by a method for specifically detecting and/or for quantifying poly(A) RNA and/or mRNA, comprising the following procedural steps:

i) contacting a poly(A)-RNA—containing sample and/or mRNA-containing sample with a poly(dT) oligonucleotide which comprises a fluorescent dye and also a quencher, with the quencher, at the emitting wavelength of the fluorescent dye, significantly quenching the fluorescence in the poly(dT) oligonucleotide both in the hybridized state and in the non-hybridized state to the same extent;

ii) hybridizing the poly(dT) oligonucleotide to the poly(A) RNA and/or mRNA, with the fluorescent signal remaining unchanged;

iii) contacting the hybridization mix from step ii) with a single-strand-specific nuclease, with fluorescently labelled nucleotides being released from those poly(dT) oligonucleotides which have not hybridized with poly(A) RNA and/or mRNA, resulting in an increase in the fluorescent signal; and iv) measuring the resulting fluorescent signal.

DETAILED DESCRIPTION OF THE INVENTION

Figure 1:
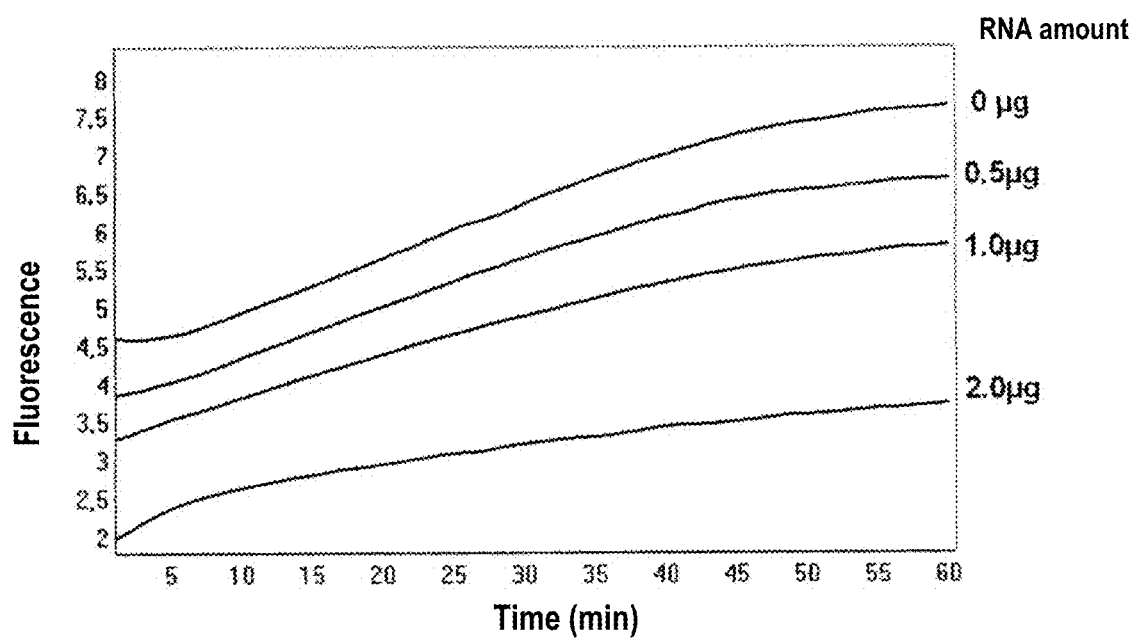
FIG. 1 is a kinetic representation of the fluorescent signal during the exonuclease I digestion for different total RNA amounts. The x-axis shows the time (in minutes); the y-axis shows the fluorescence.

The method according to the invention is suitable for specifically detecting and for quantifying all ribonucleic acids which have a region which consists of about 10 or more successive adenine ribonucleotides. These ribonucleic acids include primarily naturally occurring messenger ribonucleic acids (mRNAs), which generally have at their 3' end a poly(A) tail which consists of from about 10 to hundreds of successive adenine ribonucleotides.

Since the degradation of mRNAs often begins with the removal of the poly(A) tail at the 3' end, the method according to the invention detects and quantifies only intact, undegraded mRNA which is thus fully functional in molecular biology reactions.

In addition, the method according to the invention can also detect and quantify artificial ribonucleic acids which have at one end or within their sequence a region of about 10 or more successive adenine ribonucleotides (poly(A) RNA). These artificial ribonucleic acids can be used as, for example, an internal standard for the quantification of mRNAs when they are added at a concentration known beforehand.

When, in the method according to the invention, artificial ribonucleic acids which have a poly(A) region or natural mRNAs whose concentration is known are used in parallel reaction mixes at different concentrations, the resulting fluorescence is a function of the amount of RNA added. The higher the amount of RNA added, the lower the fluorescence which can be detected. By correlating the known amount of RNA added with the resulting fluorescence, a calibration curve can be generated. With the aid of this calibration curve, it is possible, in a reaction mix in which the amount of mRNA and/or poly(A) RNA is unknown, to determine this amount by assigning the detected fluorescence in this reaction mix with the aid of the calibration curve to an RNA amount.

The poly(dT) oligonucleotide which can be used for detecting and for quantifying mRNAs and poly(A) RNA comprises both a fluorescent dye and a quencher.

A fluorescent dye is, for the purposes of the present invention, understood to mean a dye which, after excitation at a certain wavelength, emits light of a higher wavelength.

A quencher is, for the purposes of the present invention, understood to mean a molecule which is capable of passing into an excited state via energy transfer from a fluorescent molecule and of subsequently releasing the energy again non-radiatively.

The type of quencher is chosen such that it is capable, at the emitting wavelength of the fluorescent dye, of quenching the fluorescence in the poly(dT) oligonucleotide to such an extent that a release of the fluorescent dye from the poly(dT) oligonucleotide leads to a detectable increase in fluorescence. In the method according to the invention, the quencher quenches the fluorescence of the fluorescent dye to the same extent regardless of whether the poly(dT) oligonucleotide is a free single strand or is hybridized with a further nucleic acid. The poly(dT) oligonucleotide, when it is free and not bound to a further nucleic acid, does not form a secondary structure which affects the distance between the fluorescent dye and the quencher. Thus, provided that the fluorescent dye and the quencher are present in the poly(dT) oligonucleotide, the fluorescence remains at the same level.

The distance between the fluorescent dye and the quencher in the poly(dT) oligonucleotide is chosen such that the quencher is capable of quenching the fluorescence of the fluorescent dye to such an extent that a release of the fluorescent dye from the poly(dT) oligonucleotide leads to a detectable increase in fluorescence.

In a preferred embodiment, the quencher completely quenches the fluorescence of the fluorescent dye.

The poly(dT) oligonucleotide in the method according to the invention has, in a preferred embodiment, a length in the range from 10 to 100 nucleotides.

In a particularly preferred embodiment, the poly(dT) oligonucleotide has a length in the range from 18 to 25 nucleotides.

The poly(dT) oligonucleotide according to the invention may be composed only of (dT) nucleotides. Consequently, the hybridization of the poly(dT) oligonucleotide to a poly(A) RNA or a mRNA does not result in an exact positioning of the poly(dT) oligonucleotide on these RNAs when the length of the poly(A) nucleotides in these RNAs is longer than the poly(dT) oligonucleotide. When the length of the poly(A) nucleotides is more than double the length of the poly(dT) oligonucleotide, more than one poly(dT) oligonucleotide can bind to these poly(A) nucleotides of the RNAs to be detected and to be quantified.

In a further embodiment, the poly(dT) oligonucleotide is a mixture of different poly(dT) oligonucleotides which feature at their 3' end at least one further nucleotide which is not a (dT) nucleotide. This at least one non-(dT) nucleotide at the 3' end acts as an anchor which makes sure that the poly(dT) oligonucleotide cannot hybridize to any site of the poly(A) region of the ribonucleic acid, but hybridizes exactly at the transition region between the remaining sequence of the ribonucleic acid and the poly(A) region which follows the 3' end of said sequence. The hybridization conditions in step ii) of the method according to the invention are adjusted such that the poly(dT) oligonucleotide can hybridize with its anchor region only at the transition region of the ribonucleic acid, and therefore only exactly one poly(dT) oligonucleotide can hybridize to the ribonucleic acid, regardless of how long the poly(A) region in this molecule is. A person skilled in the art is familiar with the parameters which make it possible to appropriately adjust the hybridization conditions.

The nucleotide sequence of the anchor region is not identical for all poly(dT) oligonucleotides used, but a mixture which is chosen to ensure that, in the hybridization in step ii) of the method according to the invention, exactly one poly(dT) oligonucleotide can hybridize to all mRNAs present in the sample at their transition region between poly(A) region and their remaining nucleotide sequence. It may be sufficient for the anchor region to comprise only one single nucleotide; it can, however, also comprise two or more nucleotides.

In a preferred embodiment, the distance between the fluorescent dye and the quencher in the poly(dT) oligonucleotide is a maximum of 30 nucleotides. Both the fluorescent dye and the quencher can be attached to terminal nucleotides and to nucleotides situated within the poly(dT) oligonucleotide.

In a particularly preferred embodiment, the fluorescent dye and the quencher in the poly(dT) oligonucleotide are attached to the opposite ends of the oligonucleotide. In the method according to the invention, it does not matter which of the two molecules is attached to the 5' end and which is attached to the 3' end.

In a preferred embodiment, the fluorescent dye is selected from the group comprising 6-FAM, 6-JOE, Alexa Fluor 568, Alexa Fluor 633, Alexa Fluor 680, Bodipy, CAL Fluor, CAL Fluor Red 610, TAMRA, HEX, Oregon Green, TET, Texas Red, Marina Blue, Edans Bothell Blue, Fluorescein, Yakima Yellow, Glod 540, Cy3.5 and Cy5.

In a preferred embodiment, the quencher is selected from the group comprising DABCYL, BHQ1, BHQ2 and TAMRA.

In step ii) of the method according to the invention, the poly(dT) oligonucleotide hybridizes to the poly(A) RNA and/or the mRNA which are present in the sample. Since the poly(dT) oligonucleotide inevitably does not form a secondary structure, the distance between the fluorescent dye and the quencher does not change when the poly(dT) oligonucleotide hybridizes to the target RNA, i.e. the fluorescence remains at the same constant (low) level before, during and after the hybridization step of the method according to the invention. When the quencher is chosen such that it completely quenches the fluorescence of the fluorescent dye, no fluorescence is detectable both after step i), in which the poly(dT) oligonucleotide is still present in the non-hybridized state, and after step ii), after the poly(dT) oligonucleotide has bound to the target RNA.

After the poly(dT) oligonucleotide has bound to the poly(A) RNA and/or the mRNA in step ii) of the method according to the invention, a single-strand-specific nuclease is contacted with this hybridization mix in step iii). The nuclease can already be present in the hybridization mix during the hybridization step; it can, however, also be contacted with the hybridization mix only after the hybridization is completed.

A useful single-strand-specific nuclease can be any nuclease which is capable of degrading single-stranded nucleic acids to shorter oligonucleotides or to their nucleotides, while leaving double-stranded nucleic acids intact. Useful nucleases are exonucleases which degrade the single-stranded nucleic acid starting either from its 3' end (3'→5' exonuclease) or from its 5' end (5'→3' exonuclease), and also endonucleases.

In a preferred embodiment, the single-strand-specific nuclease is selected from the group comprising exonuclease I, S1 nuclease, mung bean nuclease, exonuclease T and RecJ or a mixture of these nucleases.

In a particularly preferred embodiment, the single-strand-specific nuclease is an exonuclease, very particularly preferably exonuclease I or exonuclease T or a mixture of these exonucleases.

The single-strand-specific nuclease degrades during this step all free non-hybridized poly(dT) oligonucleotides to shorter oligonucleotides or to their single nucleotides. Since the nuclease is single-strand-specific, poly(dT) oligonucleotides which have hybridized to a poly(A) RNA and/or mRNA are not recognized by this nuclease and are, accordingly, also not degraded to shorter oligonucleotides or to their nucleotides.

Due to the degradation of the non-hybridized poly(dT) oligonucleotides to shorter oligonucleotides or to their single nucleotides, the nucleotides comprising a fluorescent dye or a quencher are also present as shorter oligonucleotides or as single nucleotides after step iii). The spatial proximity between the quencher and the fluorescent dye is then no longer provided, and so the quencher can no longer quench the emission of the fluorescent dye, and as a result, the fluorescence increases measurably.

The increase in the fluorescent signal is measured in step iv). To measure the fluorescent signal, use can be made of any analyser which is capable of emitting light of the excitation wavelength of the fluorescent dye and also of detecting light of the emission wavelength of the fluorescent dye. Useful analysers include, for example, spectrophotometers, real-time PCR cyclers and fluorescence microscopes. Further useful analysers are familar to a person skilled in the art.

The resulting fluorescent signal is higher when more non-hybridized poly(dT) oligonucleotide is present in the reaction mix. When, for different samples, the same amount of poly(dT) oligonucleotide is added in the method according to the invention, the resulting fluorescent signal is higher in the sample in which fewer poly(A) RNA and/or mRNA were present, since this sample contains more non-hybridized poly(dT) oligonucleotide, and so the samples can be quantified relative to one another.

Since the resulting fluorescent signal is higher when more poly(dT) oligonucleotide does not hybridize, the method according to the invention is suitable not only for the specific detection of poly(A) RNA and mRNA but also for their relative (see above) and absolute (see below) quantification.

By using an internal standard of artificial poly(A) RNA or of naturally occurring mRNA whose amount is known, a calibration curve of RNA concentration versus the resulting fluorescence at a constant amount of poly(dT) oligonucleotide can be generated. By comparing the fluorescence which is measured in an unknown sample with the corresponding fluorescence in the calibration curve, it is possible to determine the absolute concentration of mRNA and/or poly(A) RNA in this unknown sample.

The method according to the invention is highly suitable for rapidly and easily detecting poly(A) RNA and mRNA and also for quantifying poly(A) RNA and mRNA. This method is particularly useful for normalizing data in gene expression analyses, such as, for example, quantitative RT-PCR, microarray applications and northern blots, so that it is possible to determine in these methods the exact amount of mRNA added. Further possible uses of the method according to the invention are familiar to a person skilled in the art.

EXAMPLE

The following example is intended to further elucidate the invention without it being intended to restrict the invention to the exemplary embodiment.

Detection and quantification of RNA using poly(dT) oligonucleotides

Different amounts of total RNA (0 µg, 0.5 µg, 1 µg, 2 µg) which had been isolated beforehand from the human cell culture line HeLa were hybridized with 0.2 µM of a 22 nucleotide poly(dT) oligonucleotide labelled at the 5' end with FAM and at the 3' end with TAMRA. The hybridization mix was prepared at room temperature in a total volume of 20 µl in OmniScript RT Buffer (QIAGEN). Immediately, 20 U of exonuclease I (Epicentre) were then added to the hybridization reaction on ice and the exonuclease reaction was carried out at 25° C. in a Rotorgene 6000 real-time PCR cycler (QIAGEN) for 60 min. The resulting fluorescent signal was measured every minute at an excitation wavelength of 470 nm and a detection wavelength of 510 nm.

FIG. 1 depicts the kinetic course of the fluorescent signals during the exonuclease I digestion as a function of the total RNA amount added.

It became apparent that the sample with no RNA added generated the highest fluorescent signal, since this sample contained the highest amount of non-hybridized poly(dT) oligonucleotide. The fluorescent signal gradually decreased with increasing amounts of RNA in the sample.

This experiment shows that the method according to the invention is suitable for specifically detecting poly(A) RNA and mRNA and that only single-stranded poly(dT) oligonucleotide, which has not hybridized, is degraded by exonuclease I, but not poly(dT) oligonucleotides which are hybridized in a double strand. The experiment likewise shows that, during the first 15 min of the exonuclease I digestion, the curves for the different RNA amounts added ran parallel and that, already after 1 min of reaction time, a difference between the fluorescent signals as a function of the RNA amount added was measurable.

Figure 2:
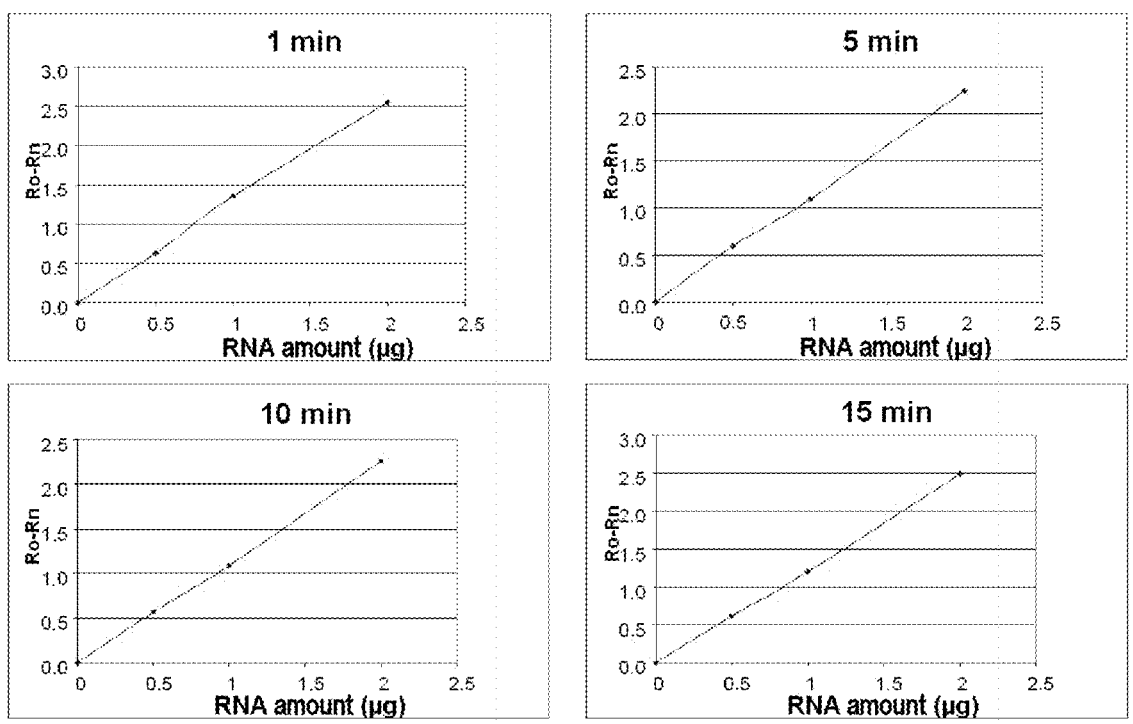
FIG. 2 shows the linear relationship between the amount of total RNA added and the resulting fluorescent signal over a course of time. The x-axis shows the amount of RNA added (in μg); the y-axis shows the fluorescent signal as the difference between the fluorescence measured without RNA (maximum fluorescence) and the fluorescence measured for the sample.

FIG. 2 shows that, for all time points measured (1 min, 5 min, 10 min, 15 min), there is a linear relationship between the RNA amount added (in µg) and the fluorescence measured. This means that, with the aid of a standard series, the amount of mRNA in an unknown sample can be reliably quantified.

Since the course of the lines for the different time points measured yielded virtually identical values in terms of the difference between the fluorescent signal without added RNA and the fluorescent signal for the respective sample with added RNA, it is also shown here that the course of the reaction is linear at least over the first 15 min and that there are no differences in the reaction rate for the RNA amounts added and that the method according to the invention is thus suited for quantifying RNA amounts in a wide concentration range.

The invention claimed is:

1. A method for specifically detecting and for quantifying ribonucleic acids having a region which comprises about 10 or more successive adenine ribonucleotides contained in a sample, the method comprising the steps of:
   i) contacting the sample with a poly(dT) oligonucleotide that is capable of hybridizing with ribonucleic acids having a region which comprises about 10 or more successive adenine ribonucleotides and that also comprises a fluorescent dye and a quencher at an emitting wavelength of the fluorescent dye to completely quench a fluorescent signal of the poly(dT) oligonucleotide to the same extent both in the hybridized state and in the non-hybridized state;

ii) hybridizing the poly(dT) oligonucleotide to the ribonucleic acids having the region which comprises about 10 or more successive adenine ribonucleotides in the sample to form a hybridization mix, with the fluorescent signal remaining unchanged;

iii) contacting the hybridization mix from step ii) with a single-strand-specific nuclease to release fluorescently labelled nucleotides from poly(dT) oligonucleotides that have not hybridized with ribonucleic acids having the region which comprises about 10 or more successive adenine ribonucleotides in the sample, resulting in an increase in the fluorescent signal; and iv) measuring the resulting fluorescent signal and comparing the measured resulting fluorescent signal with either a fluorescent signal from a different sample to relatively quantify the ribonucleic acids having the region which comprises about 10 or more successive adenine ribonucleotides contained in the sample, or a calibration curve to quantify the ribonucleic acids having the region which comprises about 10 or more successive adenine ribonucleotides contained in the sample.

2. The method according to claim 1, wherein all of the nucleotides in the poly(dT) oligonucleotide are (dT) nucleotides.

3. The method according to claim 1, wherein the sample is contacted with a mixture of different poly(dT) oligonucleotides that are capable of hybridizing with ribonucleic acids having a region which comprises about 10 or more successive adenine ribonucleotides and that also comprise a fluorescent dye and a quencher at an emitting wavelength of the fluorescent dye to completely quench a fluorescent signal of the polv(dT) oliqonucleotide to the same extent both in the hybridized state and in the non-hybridized state and which have at their 3' end at least one further nucleotide which is not a (dT) nucleotide.

4. The method according to claim 1, wherein the poly(dT) oligonucleotide has a length of up to 100 nucleotides.

5. The method according to claim 4, wherein the poly(dT) oligonucleotide has a length in the range of from 18 to 25 nucleotides.

6. The method according to claim 1, wherein the distance between the fluorescent dye and the quencher in the poly(dT) oligonucleotide is up to a maximum of 30 nucleotides.

7. The method according to claim 1, wherein the fluorescent dye is attached to a 3' end of the poly(dT) oligonucleotide and the quencher is attached to a 5' end of the poly(dT) oliqonucleotide.

8. The method according to claim 1, wherein the fluorescent dye is selected from the group consisting of 6-FAM, 6-JOE, Alexa Fluor 568, Alexa Fluor 633, Alexa Fluor 680, Bodipy, CAL Fluor, CAL Fluor Red 610, TAMRA, HEX, Oregon Green, TET, Texas Red, Marina Blue, Edans Bothell Blue, Fluorescein, Yakima Yellow, Glod 540, Cy3.5 and Cy5.

9. The method according to claim 1, wherein the quencher is selected from the group consisting of DABCYL, BHQ1 and BHQ2.

10. The method according to claim 1, wherein the single-strand-specific nuclease is an exonuclease.

11. The method according to claim 10, the exonuclease is selected from the group consisting of exonuclease I, exonuclease T, RecJ and mixtures of said exonucleases.

12. The method according to claim 11, wherein the single-strand-specific exonuclease is exonuclease I, exonuclease T or is a mixture of exonuclease I and exonuclease T.

13. The method according to claim 1, wherein the single-strand-specific nuclease is an endonuclease.

14. The method according to claim 13, wherein the single-strand-specific endonuclease is S1 nuclease, mung bean nuclease or a mixture of S1 nuclease and munq bean nuclease.

15. The method according to claim 1, wherein the quencher is attached to a 3' end of the poly(dT) oligonucleotide and the fluorescent dye is attached to a 5' end of the poly(dT) oligonucleotide.

* * * * *

UNITED STATES PATENT AND TRADEMARK OFFICE
CERTIFICATE OF CORRECTION

PATENT NO. : 8,586,304 B2
APPLICATION NO. : 13/504377
DATED : November 19, 2013
INVENTOR(S) : Fang Page 1 of 1

It is certified that error appears in the above-identified patent and that said Letters Patent is hereby corrected as shown below:

In the Claims:

Column 7, Line 36 (Claim 3, Line 8), delete "polv(dT) oliqonucleotide" and insert --poly(dT) oligonucleotide--.

Column 8, Line 12 (Claim 7, Line 4), delete "oliqonucleotide" and insert --oligonucleotide--.

Column 8, Line 34 (Claim 14, Line 3), delete "munq" and insert --mung--.

Signed and Sealed this
Eleventh Day of February, 2014

Michelle K. Lee
*Deputy Director of the United States Patent and Trademark Office*